United States Patent [19]

Aranda

[11] Patent Number: 5,362,731
[45] Date of Patent: Nov. 8, 1994

[54] USE OF PIRIBEDIL DERIVATIVES AND ANALOGS FOR THE TREATMENT OF HYPERACTIVE OR UNSTABLE BLADDERS

[76] Inventor: Bernard Aranda, 5 rue Eugène Manuel, 75116 Paris, France

[21] Appl. No.: 133,203
[22] PCT Filed: Apr. 15, 1992
[86] PCT No.: PCT/FR92/00336
§ 371 Date: Oct. 18, 1993
§ 102(e) Date: Oct. 18, 1993
[87] PCT Pub. No.: WO92/18129
PCT Pub. Date: Oct. 29, 1992

[30] Foreign Application Priority Data
Apr. 18, 1991 [FR] France ................ 91 04788

[51] Int. Cl.$^5$ .................. A61K 31/44; A61K 31/505
[52] U.S. Cl. .................... 514/255; 514/315; 514/317; 514/449; 514/452; 514/461; 514/467
[58] Field of Search .......................... 514/255

[56] References Cited

U.S. PATENT DOCUMENTS

| | | | |
|---|---|---|---|
| 4,112,093 | 9/1978 | Dumont et al. | 424/250 |
| 4,346,112 | 8/1982 | Henkel et al. | 424/325 |
| 4,742,054 | 5/1988 | Naftchi | 514/215 |
| 4,855,325 | 8/1989 | Naftchi | 514/634 |
| 4,880,634 | 11/1989 | Speiser | 424/450 |
| 5,145,852 | 9/1992 | Virag | 514/253 |

FOREIGN PATENT DOCUMENTS

| | | |
|---|---|---|
| 468875 | 1/1992 | European Pat. Off. |
| 509913 | 10/1992 | European Pat. Off. |
| 571264 | 11/1993 | European Pat. Off. |
| 2419728 | 11/1979 | France . |
| 2675383 | 4/1991 | France . |
| 2664815 | 1/1992 | France . |
| 1026517 | 1/1989 | Japan . |
| 9218129 | 10/1992 | WIPO . |

OTHER PUBLICATIONS

Patent Abstracts of Japan, vol. 13, No. 208 (C-596), 16 May 1989.
Laplane, D. "Pour la pratique . . . on retiendra . . . ", in: La Revue du Praticien, vol. 36, No. 5, 21 Jan. 1986, pp. 237–241.
Caine, M. "The importance of advenergic receptors . . . " in: Eur. Urol., vol. 3, No. 1, 1977, pp. 1–6.
Laubie, M., et al. "Inhibitory effects of piribedil . . . " in: European Journal of Pharmacology, vol. 52, 1978, pp. 99–107.
Vaidyanathan, S., et al. "Role of dopamine receptors . . . " in: Annals of Clinical Research, vol. 12, No. 1, Feb. 1980, pp. 1–4.
Raz, S., et al. "Methyldopa in treatment of neurogenic . . . " in: Urology, vol 9, No. 2, Feb. 1977, pp. 188–190.
Koyanagi, T., et al. "Reappraisal of the sympathetic role . . . " in: Investigative Urology, vol. 15, No. 4, Jan. 1978, pp. 267–269.
Che Illard, C., et al. "Prejunctional actions of piribedil . . . " in: British Journal of Pharmacology, vol. 71, No.2, pp. 513–518.
Doda, M., et al. "Dopaminergic inhibition . . . " in: Polish Journal of Pharmacology and Pharmacy, vol. 37, No. 3, 1985, pp. 397–404.

*Primary Examiner*—Shep K. Rose
*Attorney, Agent, or Firm*—Ladas & Parry

[57] ABSTRACT

Piribedil is administered to patients to treat unstable or hyperactive bladders.

9 Claims, No Drawings

USE OF PIRIBEDIL DERIVATIVES AND ANALOGS FOR THE TREATMENT OF HYPERACTIVE OR UNSTABLE BLADDERS

The present invention relates to the use of compounds, for which other applications are known, in the manufacture of a medicinal product intended for the treatment of patients having unstable or hyperactive bladders ("hyper reflexic bladder").

Unstable or hyperactive bladders are bladders which, for various reasons, result in frequent and urgent micturitions which may extend to urinary incontinence which, from a psychological and social point of view, constitutes a serious handicap.

The causes of such an instability of the detrusor may be of numerous origins, particularly due to the side effects of diseases such as brain tumors or tumors of the spinal cord, traumatic impairment of the nervous system, cerebrovascular accidents, demyelinating or degenerative diseases such as multiple sclerosis, Parkinson's disease and dementias.

The treatments known for these hyperactive bladders consist either of a treatment using compositions having antispasmodic or anticholinergic effects, such as oxybutynin chloride, imipramine or propantheline bromide, or in a surgical operation to denervate the detrusor.

The use of anticholinergic compounds, although effective, is often accompanied by many side effects, including a very extensive dryness of the mouth, which often make them difficult to accept by the patients. There are certain cases where no really acceptable treatment of this type of pathology is possible.

Accordingly, it is particularly advantageous to have demonstrated the surprising activities of compounds otherwise known for the treatment of different pathologies.

Thus, the present invention relates to the use of a compound of general formula I:

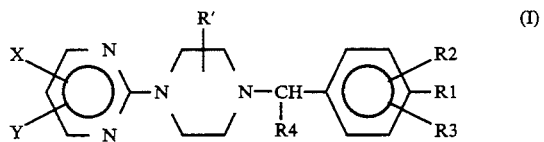

in which $R_1$, $R_2$, $R_3$, taken separately or together, may represent a hydrogen atom, a hydroxyl radical, an acetoxy group $CH_3COO-$, a $C_1$-$C_5$ lower alkoxy group or an alkylenedioxy chain $-O-(CH_2)_n-O-$ in which n may take the values 1 or 2, and $R_4$ may represent a hydrogen atom, a $C_1$-$C_5$ lower alkyl radical, or a phenyl nucleus optionally substituted by radicals or groups $R_1$, $R_2$, $R_3$, of the same type as those mentioned above, and R' represents a hydrogen atom or a methyl radical, its physiologically acceptable derivatives and its active metabolites for the manufacture of a medicinal product intended for the treatment of hyperactive bladders.

Active metabolites mean the degradation products of the compound of formula I which is active in the treatment of hyperactive bladders.

Preferably, piribedil, known in particular for its vasodilating, anti-ischemic and anti-parkinsonian properties, will be used.

Among the deviated [sic] of these products which can be used, the salts, especially methanesulfonate for piribedil, should be mentioned.

Taking into account the pathology to be treated, the most suitable galenical forms are the oral forms, especially tablets, as well as the delayed-action galenical forms, especially the transdermal forms.

The tablets generally contain doses of between 15 and 60 mg of compound of general formula I.

The injectable forms are also preferred for an intravenous or parenteral administration.

The forms and the doses which can be used may vary between 1 to 15 mg/kg per day of active ingredient, it being possible for these doses to be adjusted according to the condition of the patient and the extent of the disorder, as well as the progression of his condition.

The examples below make it possible to demonstrate other characteristics and advantages of the present invention.

EXAMPLE 1

Procedure for Carrying Out the Piribedil Test

Piribedil is provided in the form of an injectable solution of 0.003 g/ml of piribedil methanesulfonate. On the eve of the test, the patient optionally stops taking antiparkinsonian drugs, and ingests three times 20 mg of domperidone, 20 mg dose repeated the next morning 2 hours before the test.

A perfusion is then fitted and a cystomanometry and a reference urethral profile are performed.

During the course of the entire test, the arterial constancy is monitored. The piribedil solution is very slowly injected intravenously.

A cystomanometry is performed every 5 min to 10 min for 30 minutes. In particular, a cystomanometry should be performed as soon as yawning and somnolence appear.

This test was performed on six patients having a hyperactive bladder associated either with Parkinson's disease (I, II, III, and IV), or with a multiple sclerosis (V and VI).

The results of the different tests show in particular for patient III by cystomanometry an increase in the bladder capacity from 180 to 260 cm³ and for patient IV from 290 to 550 cm³.

Following these tests, it was decided to treat patient VI by oral administration of tablets containing 0.05 g of piribedil per tablet. This patient was treated for 6 months at the dose of 6 tablets per day. The surprising results show a clear clinical improvement with a reduction in urinary incontinence and, after 6 months, a bladder of which the capacity is stabilized at about 450 cm³, whereas a reference measurement before the treatment had shown a limit of 220 cm³.

In view of these results, new tests were performed on thirty-five patients for the intravenous tests and on sixty other patients treated with piribedil in the form of tablets.

EXAMPLE II

Piribedil Test

The procedure followed is identical to that described in Example I.

The administration of domperidone is not essential for carrying out the test and is used only when the patient shows risks of vomiting.

Thirty-five patients with a hyperactive bladder were explored by intravenous tests using piribedil, comprising a cystomanometry before injection followed by a series of cystomanometries after slow intravenous injection of 3 mg of piribedil.

The pathologies of these patients were: Parkinson's disease, multiple sclerosis, neurovascular affections, impairment of the terminal cone and traumatic lesions of the spinal cord, peripheral neuropathy, cranial trauma victims, idiopathic vesical instability.

In 23 cases (66%), the test was positive: increase in the vesical capacity of 30% or more relative to the vesical capacity before injection. In 7 of these cases, the increase in the vesical capacity was greater than 50% (highly positive test).

In 12 cases (33%), the test was negative. These negative tests were essentially represented by patients suffering from a traumatic medullary lesion (8 patients out of 12).

EXAMPLE III

Patients having been Treated with Piribedil per os in the Form of Tablets Containing Doses of 20 mg or 50 mg.

Sixty patients with a hyperactive bladder were monitored for 1 to 6 months in an open study, with daily piribedil doses of between 60 and 300 mg.

The relevant pathologies were: Parkinson's disease, multiple sclerosis, neurovascular affections, impairment of the terminal cone and traumatic lesions of the spinal cord, peripheral neuropathy, cranial trauma victims, idiopathic vesical instability, infant enuresis.

The treatment provided a benefit in 44 cases (73%): disappearance or reduction of leakages, improved possibility of retention, reduction of enuresis, reduction of pollakiuria. The treatment did not have any effect in 12 cases (20%).

The treatment had to be interrupted in 4 cases because of intolerable side effects (nausea, vomiting, vertigo). Otherwise, the side effects were sometimes inconvenient initially in 11 cases, without resulting in the interruption of the treatment or sometimes simply a reduction of the doses. The administration of domperidone was necessary in the long term in order to prevent vomiting in some patients (7 cases).

I claim:

1. A method of treating a hyperactive or unstable bladder in a patient afflicted therewith comprising administering thereto an effective amount of a compound of general formula I:

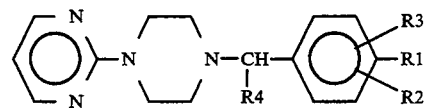

in which $R_1$, $R_2$, $R_3$, taken separately or together, may represent a hydrogen atom, a hydroxyl radical, an acetoxy group $CH_3COO$—, a $C_1$–$C_5$ lower alkoxy group or an alkylenedioxy chain —O— $(CH_2)_n$—O— in which n may take the values 1 or 2, and $R_4$ may represent a hydrogen atom, a $C_1$–$C_5$ lower alkyl radical, or a phenyl nucleus optionally substituted by radicals or group $R_1$, $R_2$, $R_3$, of the same type as those mentioned above, and $R'$ represents a hydrogen atom or a methyl radical, its physiologically acceptable derivatives and its active metabolites for the manufacture of a medicinal product intended for the treatment of hyperactive or unstable bladders.

2. The bladder-treating method according to claim 1, characterized in that the compound of general formula I is piribedil or its physiologically acceptable salts.

3. The bladder-treating method according to claim 2, characterized in that the compound of general formula I is piribedil methane-sulfonate.

4. The bladder-treating method according to claim 1, characterized in that the medicinal product intended for the treatment of hyperactive bladders is a medicinal product in a form which is suitable for oral, intravenous or parenteral administration.

5. The bladder-treating method according to claim 4, characterized in that the medicinal product is in the form of a tablet.

6. The bladder-treating method according to claim 5, characterized in that the tablet contains a dose of between 15 and 60 mg of compound of general formula I.

7. The bladder-treating method according to claim 4, characterized in that the medicinal product is in an injectable form.

8. The bladder-treating method according to claim 2, characterized in that the medicinal product intended for the treatment of hyperactive bladders is a medicinal product in a form which is suitable for oral, intravenous or parenteral administration.

9. The bladder-treating method according to claim 3, characterized in that the medicinal product intended for the treatment of hyperactive bladders is a medicinal product in a form which is suitable for oral, intravenous or parenteral administration.

* * * * *